(12) United States Patent
Yamka et al.

(10) Patent No.: US 8,557,869 B2
(45) Date of Patent: *Oct. 15, 2013

(54) COMPOSITIONS AND METHODS FOR PROMOTING FAT LOSS

(75) Inventors: Ryan Michael Yamka, Topeka, KS (US); Kim Gene Friesen, Carthage, IN (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 888 days.

This patent is subject to a terminal disclaimer.

(21) Appl. No.: 12/535,893

(22) Filed: Aug. 5, 2009

(65) Prior Publication Data

US 2010/0029768 A1      Feb. 4, 2010

Related U.S. Application Data

(62) Division of application No. 11/621,888, filed on Jan. 10, 2007.

(60) Provisional application No. 60/758,274, filed on Jan. 10, 2006.

(51) Int. Cl.
*A61K 31/195*     (2006.01)
*C07C 229/26*     (2006.01)

(52) U.S. Cl.
USPC .......................... 514/564; 562/562

(58) Field of Classification Search
None
See application file for complete search history.

(56) References Cited

U.S. PATENT DOCUMENTS

| | | | |
|---|---|---|---|
| 5,650,418 A | | 7/1997 | Rath et al. |
| 6,541,026 B2 * | | 4/2003 | Siskind .......................... 424/439 |
| 7,470,439 B1 | | 12/2008 | Nizio et al. |
| 2004/0081743 A1 * | | 4/2004 | Laflamme et al. ............ 426/630 |
| 2005/0249781 A1 * | | 11/2005 | Hirabayashi et al. ......... 424/439 |

FOREIGN PATENT DOCUMENTS

| | | |
|---|---|---|
| JP | 2000-001440 A | 1/2000 |
| JP | 2005-312365 A | 11/2005 |
| WO | WO 02/13624 | 2/2002 |
| WO | WO 03/016441 | 2/2003 |
| WO | WO 2004/037011 | 5/2004 |

OTHER PUBLICATIONS

Center et al. J Vet Intern Med, 598-608, 2000.*
Cheng et al. J Appl Poultry Res 6, 1-17, 1997.*
Defintion of "food" from dictionary.com, accessed Dec. 5, 2012.*
AAFCO, 2004, Official Publication of the Association of American Feed Control Officials, pp. 137-140.
Alomar et al., 2006, "Nutritional Evaluation of Commercial Dry Dog Foods by Near Infrared Reflectance Spectroscopy," J. Animal Physiol. Animal Nutr. 90(5-6):223-229.
Anderson et al., 1979, "Lysine and Arginine Requirements of the Domestic Cat," J. Nutrition 109(8):1368-1372.
Hand et al., eds., 2000, *Small Animal Clinical Nutrition*, 4th edition, Walsworth Publishing Co., Marceline, MO, pp. 127-146 and 402-407.
International Search Report and Written Opinion in International Application No. PCT/US07/060327, mailed Apr. 4, 2007.
Laflamme et al., 2005, "Increased Dietary Protein Promotes Fat Loss and Reduces Loss of Lean Body Mass During Weight Loss in Cats," Intern. Appl. Res. Vet. Med. 3(2):62-68.
Morris et al., 2004, "Lysine Requirement of Kittens Given Purified Diets for Maximal Growth," J. Animal Physiol. Animal Nutr. 88(3-4):113-116.
Xavier et al., 1998, *Clinical Guidelines of the Identification, Evaluation and Treatment of Overweight and Obesity in Adults*, National Institutes of Health, NIH Publication No. 98-4083.

* cited by examiner

*Primary Examiner* — Nissa Westerberg
(74) *Attorney, Agent, or Firm* — Thomas M. Hunter

(57) ABSTRACT

This invention provides diets useful for promoting fat loss in animals having a total lysine to metabolizable energy ratio of from about 6 to about 10 g/Mcal. This invention also provides compositions for promoting fat loss in animals, methods for preparing the compositions, methods for using the diets and compositions, articles of manufacture comprising the diets and compositions, and means for communicating information or instructions about such diets, compositions, methods, and articles of manufacture.

5 Claims, No Drawings

COMPOSITIONS AND METHODS FOR PROMOTING FAT LOSS

This application claims benefit of U.S. Provisional No. 60/758,274 filed Jan. 10, 2006 and is a Divisional application of Ser. No. 11/621,888, filed Jan. 10, 2007, which is hereby incorporated by reference in its entirety for all purposes.

BACKGROUND OF THE INVENTION

1. Field of the Invention

This invention relates generally to diets for promoting weight loss in animals, and, more particularly to diets for promoting fat loss in adult animals. This invention also relates to compositions for promoting fat loss in adult animals, methods for preparing such compositions, methods for using such diets and compositions, articles of manufacture comprising such diets and compositions, and means for communicating information about such diets, compositions, methods, and articles of manufacture.

2. Description of the Related Art

Overweight and obese animals accumulate excessive quantities of body fat. Excessive body fat and weight are related as body weight increases when fat accumulates. While body weight can increase from the accumulation of any tissue or fluid, the majority of overweight animals are overweight due to the accumulation of excess body fat.

Excess body fat has detrimental effects on health and longevity, and obesity has been associated with numerous diseases such as, for example, hypertension, degenerative joint and orthopedic disease, cardiovascular disease, and heat intolerance. Thus, strategies for fat loss and overall weight management are very important for both the short- and long-term health of animals and overweight and obese animals in particular.

Different treatment strategies attempt to address fat loss and weight management. Some such strategies focus on reducing the amount of fat in foods. Because fat has about 2.25 times the calories of an equivalent weight of carbohydrate or protein, reduced fat foods have decreased caloric density. However, reduced fat foods typically are less palatable than calorically dense foods. In addition, consumption of reduced fat foods typically contributes to poor skin and/or pelage quality.

Other weight and fat loss strategies focus on increasing the amount of fiber in foods while reducing the amount of fat. Dietary fiber can facilitate weight loss by diluting calories, limiting food consumption as a result of more bulk being present in the gastrointestinal tract, increasing satiety, and/or decreasing the availability of calories by interfering with the digestion of fat, protein, and soluble carbohydrate. Reduced fat/high fiber foods typically are less palatable than calorically dense foods. In addition, reduced fat/high fiber foods typically have lower digestibility and also can cause gastric distress.

Yet other weight and fat loss strategies focus on increasing the amount of protein and fat in foods while limiting or altogether excluding carbohydrates. These strategies are based on the theory that overweight animals eat too many carbohydrates. While both carbohydrates and fats are burned for energy, carbohydrates are used first. The premise is that when the intake of carbohydrates is drastically reduced bodies will naturally lose weight by burning stored fat more efficiently. There has been a discussion about the short- and long-term risks of no- or low-carbohydrate diets. In addition, such diets have delivered nixed results.

Thus, there is a need for alternative compositions and methods for promoting fat loss in animals, particularly in overweight and obese adult animals.

SUMMARY OF THE INVENTION

It is an object of this invention to provide diets for promoting fat loss in adult animals.

It is another object to provide compositions for promoting fat loss in adult animals.

It is another object to provide methods for promoting fat loss in adult animals.

It is another object to provide articles of manufacture comprising a composition of this invention or two or more ingredients that, when combined together and, optionally, with additional ingredients that are or are not a part of the article of manufacture, yield a composition of this invention.

It is another object of the invention to provide means for communicating information about the compositions, methods, and articles of manufacture of this invention.

One or more of these and other objects can be achieved by using compositions that have a total lysine to metabolizable energy ratio of from about 6 to about 10 g/Mcal and/or by feeding diets that have a total lysine to metabolizable energy ratio of from about 6 to about 10 g/Mcal.

Additional objects, features, and advantages of the invention will be apparent to those skilled in the art.

DETAILED DESCRIPTION OF THE INVENTION

In one aspect, the present invention provides a method for promoting fat loss in an adult animal. In some embodiments, the animal can lose weight without losing any lean muscle mass. In other embodiments, the animal can lose fat and at the same time increase the amount of its lean muscle mass. The method is suitable for promoting fat loss in adult animals that have optimal body weight, but it is desired that they lose fat. In such cases, it is typically desired that the animals lose a relatively small amount of fat, and, optionally, gain lean muscle mass. The method is also suitable for promoting fat loss in overweight as well as obese adult animals. In such cases, typically it is desired that the overweight animals lose as much fat as is needed to have optimal body weight, and that the obese animals lose as much fat as is needed to at least become less obese. Ideally, it is desired that both the overweight and the obese animals lose as much fat as they need to lose to come back to a fat level that is considered normal for such animals, and, optionally, to maintain their lean muscle mass or gain additional lean muscle mass while losing fat.

As discussed above, the method for promoting fat loss of this invention is suitable for adult animals. An adult animal is one of any age after the completion of juvenile growth and development, including senior and geriatric animals. For example, in the case of cats and dogs this typically means an age of about 1 year through the remainder of their life. A senior animal is one of an age having an increased risk for age-related disease which may but need not have obvious physical or behavioral characteristics of aging. Typically, but also depending on breed, a senior dog is one of about 7 through about 9 years of age, a senior large breed dog is one of about 5 years of age and beyond, and a senior cat is one of about 7 through about 11 years of age. A geriatric animal is one showing typical outward signs of aging, such as arthritis, gray hair, etc. for example, a dog of about 10 years of age and beyond, a large breed dog of about 7 years of age and beyond, or a cat of about 12 years of age and beyond.

In some embodiments, the animal is a member of the order Carnivora. In some such embodiments, the animal is a canine, and in other such embodiments the animal is a feline. The method of promoting fat loss of this invention is also suitable for other animals, including humans as well as nonhuman animals, for example, non-human primates (e.g., chimpanzees and monkeys), companion and working animals (e.g., horses), farm animals (e.g., goats, sheep, pigs, and cattle), and wild and zoo animals (e.g., wolves, bears, and deer). The method of promoting fat loss of this invention is also suitable for non-mammalian animals, for example, companion, farm, zoo, and wild birds (e.g., song birds, parrots, ducks, geese, turkeys, chickens, and ostriches).

In some embodiments, the animal is a companion animal. A companion animal can be, for example, an animal of any species that is kept as a pet. A companion animal can also be an animal from a variety of widely domesticated species, for example, dogs (Canis familiaris) and cats (Felis domesticus) regardless of whether or not the animal is kept solely as a pet. Thus, companion animals include, for example, working dogs, farm cats as well as pet cats and dogs.

In some embodiments, the animal is overweight. And in some such embodiments, the animal is obese. An overweight animal has an increased body weight as a result of an excessive accumulation of fat. An overweight animal typically weighs about 10 to about 19% more than its optimal body weight, and an obese animal typically weighs at least about 20% more than its optimal body weight.

People skilled in the art use different methods to define overweight and obesity. See, for example, Small Animal Nutrition, pages 402-407 (2005). Actual body weight relative to optimal weight can be used as a defining criterion for obesity because body weight is easier to measure than body fat. Using this method, people typically are defined as obese when actual body weight exceeds optimal body weight by about 15 to about 30%. Cats and dogs that are about 10 to about 19% over optimal weight are considered overweight; and cats and dogs that are about 20% over optimal weight are considered obese. Fat expressed as a percentage of body weight can also be used to define obesity. People are considered obese when their percent body fat exceeds about 20 to about 30% of total weight. Body composition studies of dogs and cats indicate that animals judged to be in optimal body condition have about 15 to about 20% body fat. Overweight can also be defined as a body mass index (BMI) in humans of 25 to 29.9 kg/m$^2$ and obesity defined as a BMI of 30 kg/m$^2$ or greater. Such definitions are well known to skilled artisans, See Clinical Guidelines on the Identification, Evaluation, and Treatment of Overweight and Obesity in Adults, NIH Publication No 98-4083, September 1998. For the purposes of this invention, an animal will be considered overweight or obese if one skilled in the art, e.g., a health care provider, has determined that the animal is overweight and/or obese regardless of the method that the skilled artisan uses.

The method for promoting fat loss of this invention comprises feeding the animal a diet that has a total lysine to metabolizable energy of from about 6 to about 10 g/Mcal.

An animal's diet includes everything consumed by the animal. Thus, an animal's diet can comprise one or more compositions. A composition consumed by an animal can be, for example, a food composition. In some embodiments, such composition meets the minimum nutrient level requirements for reproduction or maintenance recommended by the Association of American Feed Control Officials (AAFCO). See 2005 Official Publication of the AAFCO, pages 137-140. In some embodiments, the food composition can comprise a dry food. In some embodiments, the food composition can comprise a moist food. In some embodiments, the food composition can comprise a semi-moist food. In some embodiments, a composition which is a part of the animal's diet can comprise a supplement, treat, snack, or partially or fully edible toy. In some embodiments, a composition which is a part of the animal's diet can comprise a mixture of one or more foods.

Lysine is an essential amino acid required in an animal's diet for balanced nutrition. The values for the total amount of lysine (and the total amounts of other amino acids) provided by the invention are determined using amino acid analysis methods 988.15 (regular and sulfur-containing amino acids) and 994.12 (tryptophan) established by the Association of Official Analytical Chemists. See Official Methods of Analysis (1995).

Metabolizable energy (ME) of a diet (or of a composition if the diet consists of a single composition) is the energy available to an animal upon consumption of the diet (or composition) after subtracting the energy excreted in feces, urine, and combustible gases. Metabolizable energy values are determined following the protocols established by AAFCO.

The total lysine to metabolizable energy ratio is the total amount of lysine present in a diet (or composition) relative to the metabolizable energy content of the diet (or composition). A typical canine or feline diet as contemplated herein may contain 2000 to 5000 kcal/kg metabolizable energy. Those skilled in the art can determine the total lysine to metabolizable ratio of diets including two or more compositions. And those skilled in the art also understand that if an animal's diet consists of a single composition, then the total lysine to metabolizable energy ratio of the diet is equal to the total lysine to metabolizable energy ratio of that composition. Such a composition will be suitable for the method for promoting fat loss of this invention if it has a total lysine to metabolizable energy ratio of from about 6 to about 10 g/Mcal. In some embodiments, the method for promoting fat loss comprises feeding the animal a single composition that has a total lysine to metabolizable energy ratio of from about 6 to about 10 g/Mcal until, for example, the animal loses a desired amount of fat. In other embodiments, different compositions that each have a total lysine to metabolizable energy ratio of from about 6 to about 10 g/Mcal are fed to the animal for varying time intervals.

In some embodiments of the method for promoting fat loss of this invention, the diet comprises a composition that has a total lysine to metabolizable energy ratio of from about 6 to about 10 g/Mcal. In some such embodiments, the diet consists of a composition that has a total lysine to metabolizable energy ratio of from about 6 to about 10 g/Mcal.

In some embodiments of the method for promoting fat loss, the diet has a total lysine to metabolizable energy ratio of from about 6 to about 8 g/Mcal. In some such embodiments, the diet has a total lysine to metabolizable energy ratio of from about 6 to about 7.5 g/Mcal. In other such embodiments, the diet has a total lysine to metabolizable energy ratio of from about 6 to about 7 g/Mcal. In further such embodiments, the diet has a total lysine to metabolizable energy ratio of from about 6 to about 6.5 g/Mcal. As discussed above, the diet can comprise one or more compositions.

In some embodiments of the method for promoting fat loss, the diet also comprises arginine in a total arginine to total lysine ratio of about 0.6 to about 1.4. Arginine is an essential amino acid required in an animal's diet for balanced nutrition. The total arginine to total lysine ratio is the amount of arginine present in the diet relative to the total amount of lysine present in the diet. In some embodiments, the diet comprises an amount of arginine that is equal to or higher than AAFCO's minimum recommended allowances for reproduction and maintenance. In some such embodiments, the diet comprises an amount of arginine that is up to about 100% higher, up to about 150% higher, up to about 200% higher, up to about 250% higher, up to about 300% higher, up to about 350% higher, up to about 400% higher, or up to about 450% higher than the AAFCO's minimum allowances for reproduction and maintenance. The AAFCO's minim arginine allowances for reproduction and maintenance for dogs are 0.62% and 0.51%, respectively (presuming energy density of the diet of 3.5 kcal ME/g dry matter). AAFCO's minimum argutine allowances for reproduction and maintenance for cats are 1.25% and 1.04%, respectively (presuming energy density of the diet of 4.0 kcal ME/g dry matter). In some embodiments, the diet comprises arginine in a total arginine to total lysine amount of about 0.6 to about 1. In some embodiments, the diet comprises arginine in a total arginLine to total lysine amount of about 0.8 to about 1.2. In some embodiments, the diet comprises arginine in a total arginine to total lysine amount of about 0.7 to about 1.1.

In some embodiments of the method for promoting fat loss, the diet also comprises leucine in a total leucine to total lysine ratio of about 0.9 to about 2.2. Leucine is an essential branched amino acid required in an animal's diet for balanced nutrition. The total leucine to total lysine ratio is the amount of leucine present in the diet relative to the total amount of lysine present in the diet. In some embodiments, the diet comprises an amount of leucine that is equal to or higher than the AAFCO's minimum recommended allowances for reproduction and maintenance. In some such embodiments, the diet comprises an amount of leucine that is up to about 100% higher, up to about 150% higher, up to about 200% higher, up to about 250% higher, up to about 300% higher, up to about 350% higher, up to about 400% higher, up to about 450% higher, up to about 500% higher, up to about 600% higher, up to about 700% higher, up to about 750% higher, or up to about 800% higher than the AAFCO's minimum allowances for reproduction and maintenance. The AAFCO's minimum leucine allowances for reproduction and maintenance for dogs are 0.72% and 0.59%, respectively (presuming energy density of the diet of 3.5 kcal ME/g dry matter). The AAFCO's mininium leucine allowances for reproduction and maintenance for cats are 1.25% (presuming energy density of the diet of 4.0 kcal ME/g dry matter). In some embodiments, the diet comprises leucine in a total leucine to total lysine amounit of about 0.9 to about 1.4. In some embodiments, the diet comprises leucine in a total leucine to total lysine amount of about 1.6 to about 2. In some embodiments, the diet comprises leucine in a total leucine to total lysine amount of about 0.9 to about 1.9.

In some embodiments of the method for promoting fat loss, the diet also comprises isoleucine in a total isoleucine to total lysine ratio of about 0.2 to about 1. isoleucine is an essential branched amino acid required in an animal's diet for balanced nutrition. The total isoleucine to total lysine ratio is the amount of isoleucine present in the diet relative to the total amount of lysine present in the diet. In some embodiments, the diet comprises an amount of isoleucine that is equal to or higher than the AAFCO's minimum recommended allowances for reproduction and maintenance. In some such embodiments, the diet comprises an amount of isoleucine that is up to about 100% higher, up to about 150% higher, or up to about 200% higher than AAFCO's minimum allowances for reproduction and maintenance. The AAFCO's minimum isoleucine allowances for reproduction and maintenance for dogs are 0.45% and 0.37% respectively (presuming energy density of the diet of 3.5 kcal ME/g dry matter). The AAF-CO's minimum isoleuciue allow %ances for reproduction and maintenance for cats are 0.52% (presuming energy density of the diet of 4.0 kcal ME/g dry matter). In some embodiments, the diet comprises isoleucine in a total isoleucine to total lysine amount of about 0.2 to about 0.6. In some embodiments, the diet comprises isoleucine in a total isoleucine to total lysine amount of about 0.5 to about 1. In some embodiments, the diet comprises isoleucine in a total isoleucine to total lysine amount of about 0.3 to about 0.7.

In some embodiments of the method for promoting fat loss, the diet also comprises valine in a total valine to total lysine ratio of about 0.4 to about 1.2. Valine is an essential branched amino acid required in an animal's diet for balanced nutrition. The total valine to total lysine ratio is the amount of valine present in the diet relative to the total amount of lysine present in the diet. In some embodiments, the diet comprises an amount of valine that is equal to or higher than the AAFCO's minimum recommended allowances for reproduction and maintenance. In some such embodiments, the diet comprises an amount of valine that is up to about 100% higher, up to about 150% higher, up to about 200% higher, up to about 250% higher, up to about 300% higher, up to about 350% higher, up to about 400% higher, or up to about 450% higher than the AAFCO's minimum allowances for reproduction and maintenance. The AAFCO's minimum valine allowances for reproduction and maintenance for dogs are 0.48% and 0.39%, respectively (presuming energy density of the diet of 3.5 kcal ME/g dry matter). AAFCO's minimum valine allowances for reproduction and maintenance for cats are 0.62% (presuming energy density of the diet of 4.0 kcal ME/g dry matter). In some embodiments, the diet comprises valine in a total valine to total lysine amount of about 0.4 to about 0.8. In some embodiments, the diet comprises valine in a total valine to total lysine amount of about 0.6 to about 1. In some embodiments, the diet comprises valine in a total valine to total lysine amount of about 0.4 to about 0.9.

In some embodiments of the method for promoting fat loss, the diet comprises one or more of arginine, leucine, isoleucine, and valine in amounts as discussed above. In some such embodiments, the diet comprises arginine, leucine, isoleucine, and valine in a total arginine plus leucine plus isoleucine plus valine to total lysine ratio of from about 3 to about 6. The total arginine plus leucine plus isoleucine plus valine to total lysine ratio is the amount of arginine plus leucine plus isoleucine plus valine present in the diet relative to the total amount of lysine present in the diet. In some such embodiments, the total arginine plus leucine plus isoleucine plus valine to total lysine ratio of from about 3 to about 5.

In some cases, it may be desirable to feed a diet of this invention (including a diet that consists of a single composition) to the animal in conjunction with the administration of one or more agents that can increase the animal's lean muscle mass. Similarly, it may be desirable to feed a diet of this invention to the animal in conjunction with the administration of one or more agents that can help the animal reduce fat gain. In addition, if the animal suffers from one or more diseases, it may be needed to feed a diet of this invention to the animal in conjunction with the administration of one or more agents that can help promote the animal's health.

Thus, in some embodiments, the method for promoting fat loss further comprises administering to the animal one or more agents for increasing lean muscle mass, reducing fat gain, and/or promoting the health or wellness of the animal. Health refers to the absence of disease or infirmity. Wellness refers to the complete physical, mental, and social wellbeing of the animal, not merely the absence of infirmity. The term "in conjunction" means that an agent is administered to the animal either together with a diet (including a particular composition that is a part of the diet) of this invention or separately from the diet or composition at the same or different frequency via the same or different administration route and either at about the same time as the diet or composition or periodically. "About at the same time" generally means that an agent is administered to an animal when a diet or composition of this invention is fed to the animal or within about 72 hours of feeding the diet or composition to the animal. "Periodically" generally means that an agent is administered to an animal following a dosage schedule suitable for administering that agent while a diet or composition of the invention is fed to the animal routinely as appropriate for that animal. Thus, the term "in conjunction" specifically includes situations when an agent is administered to an animal for a prescribed period of time while a diet or composition is fed to the animal until it, for example, loses a desired amount of fat. If two or more agents are to be administered to an animal, the dosage schedule and route of administration for each agent may vary. In addition, one diet or composition of the invention may be substituted with another diet or composition of the invention while a specific agent is administered to the animal.

In some embodiments, the agent for increasing lean muscle mass and/or reducing fat gain comprises carnitine. Carnitine, or L-carnitine, is a vitamin-like compound synthesized in the body from lysine and methionine. Carnitine attaches to long-chain fatty acids and transports them into cellular mitochondria where the fatty, acids are broken down through oxidation and converted to energy for all tissues including the skeletal muscles, heart, and liver. Through this process, carnitine helps reduce storage of body fat and the amount of fat in the blood stream.

In some embodiments, the agent for increasing lean muscle mass and/or reducing fat gain comprises chromium. Chromium is a trace element and a cofactor for insulin which, in turn, regulates the metabolism of proteins, fats, and carbohydrates. Chromium helps an animal lose body fat, retain and build lean body mass, lower elevated blood sugar, and reduce blood cholesterol levels. Administering chromium as chromium picolinate or chromium polynicotinate may facilitate the absorption of chromium in the digestive system.

An agent for promoting health or wellness can, for example, improve an animal's cognitive functions or the appearance and thickness of an animal's hair or coat, or can ameliorate or treat a disease that the animal suffers from.

In some embodiments, the agent for promoting health or wellness comprises one or more antioxidants. An antioxidant is a nutrient or non-nutrient substance that prevents the formation of, or quenches, free radicals. Vitamin E, for example, works in conjunction with glutathione peroxidase to protect cells against the adverse effects of reactive oxygen and other free radicals that initiate the oxidation of polyunsaturated membrane phospholipids. Vitamin E can be administered in the form of an $\alpha$-, $\beta$-, $\gamma$-, or $\delta$-tocopherol, $\alpha$-, $\beta$-, $\gamma$-, or $\delta$-tocotrienol, or a mixture of any of those isomeric forms. Another antioxidant, vitamin C, protects against free radical damage induced by the oxidative burst of neutrophils and stimulates the phagocytic effect of leukocytes, thus playing a role in immune function. Vitamin C (and L-ascorbic acid in particular) can be administered, for example, in the form of a salt or ester such as sodium, calcium, zinc, or ferrous salt or stearate or palmitate ester.

In some embodiments, the agent for promoting health or wellness comprises one or more essential fatty acids such as, for example, omega-6 or omega-3 fatty acids. Omega-6 essential fatty acids include, for example, linoleic acid and arachidonic acid; and omega-3 essential fatty acids include, for example, alpha-linolenic acid, eicosapentaenoic acid, and docosahexaenoic acid. Essential fatty acids serve as substrates that may be metabolized to form important, biologically active compounds. Arachidonic acid, gamma-linolenic acid, and eicosapentaenoic acid act as precursors for the synthesis of eicosanoids, an important group of immunoregulatory molecules that function as local hormones and mediators of inflammation. Linoleic acid incorporates into the ceramides of the epidermal cornified envelope, which serves an essential barrier function to prevent loss of water and other nutrients from the skin. Essential fatty acids may be used in the form of various derivatives, for example, salts of inorganic and organic acids, phospolipid esters, ethers, and sterol derivatives. Linoleic and linolenic acids can be used as, for example, phosphatidal choline esters, phosphatidal ether, and sipolsterol ester.

In another aspect, the present invention provides diets and compositions suitable for promoting fat loss in an adult animals. These diets and compositions are described above in the context of the method for promoting fat loss in an adult animal. More specifically, a diet of this invention is a diet that has a total lysine to metabolizable energy ratio of from about 6 to about 10 g/Mcal. As discussed above, if the diet comprises more than one composition, the total lysine to metabolizable ratio of the diet is determined by accounting for the amounts of lysine and metabolizable energy present in all those compositions.

In addition, as discussed above, if a diet of this invention consists of a single composition, then that composition has a total lysine to metabolizable energy ratio of from about 6 to about 10 g/Mcal. In some embodiments, the composition has a total lysine to metabolizable energy ratio of from about 6 to about 8 g/Mcal. In some such embodiments, the composition has a total lysine to metabolizable energy ratio of from about 6 to about 7.5 g/Mcal. In other such embodiments, the composition has a total lysine to metabolizable energy ratio of from about 6 to about 7 g/Mcal. In further such embodiments, the composition has a total lysine to metabolizable energy ratio of from about 6 to about 6.5 g/Mcal.

In some embodiments, the composition also comprises arginine in a total arginine to total lysine ratio of about 0.6 to about 1.4. In some embodiments, the composition comprises arginine in a total arginine to total lysine amount of about 0.6 to about 1. In some embodiments, the composition comprises arginine in a total arginine to total lysine amount of about 0.8 to about 1.2. In some embodiments, the diet comprises arginine in a total arginine to total lysine amount of about 0.7 to about 1.1.

In some embodiments, the composition also comprises leucine in a total leucine to total lysine ratio of about 0.9 to about 2.2. In some embodiments, the composition comprises leucine in a total leucine to total lysine amount of about 0.9 to about 1.4. In some embodiments, the composition comprises leucine in a total leucine to total lysine amount of about 1.6 to about 2. In some embodiments, the composition comprises leucine in a total leucine to total lysine amount of about 0.9 to about 1.9.

In some embodiments, the composition also comprises isoleucine in a total isoleucine to total lysine ratio of about 0.2 to about 1. In some embodiments, the composition comprises isoleucine in a total isoleucine to total lysine amount of about 0.2 to about 0.6. In some embodiments, the composition comprises isoleucine in a total isoleucine to total lysine amount of about 0.5 to about 1. In some embodiments, the composition comprises isoleucine in a total isoleucine to total lysine amount of about 0.3 to about 0.7.

In some embodiments, tie composition also comprises valine in a total valine to total lysine ratio of about 0.4 to about 1.2. In some embodiments, the composition comprises valine in a total valine to total lysine amount of about 0.4 to about 0.8. In some embodiments, the composition comprises valine in a total valine to total lysine amount of about 0.6 to about 1. In some embodiments, the composition comprises valine in a total valine to total lysine amount of about 0.4 to about 0.9.

In some embodiments, the composition comprises one or more of arginine, leucine, isoleucine, and valine in amounts as discussed above. In some such embodiments, the composition comprises arginine, leucine, isoleucine, and valine in a total arginine plus leucine plus isoleucine plus valine to total lysine ratio of from about 3 to about 6. The total arginine plus leucine plus isoleucine plus valine to total lysine ratio is the amount of arginine plus leucine plus isoleucine plus valine present in the composition relative to the total amount of lysine present in the composition. In some such embodiments, the total arginine plus leucine plus isoleucine plus valine to total lysine ratio of from about 3 to about 5.

In a further aspect, the invention provides methods for preparing compositions that are suitable for use in the methods for promoting fat loss discussed above. Such compositions can be prepared, for example, by mixing two or more ingredients (including food compositions) that, when combined, yield a composition of the invention or by mixing one or more food compositions with additional ingredient(s), for example, amino acids. Such compositions can be prepared by one or more of the methods discussed in, for example, Small Animal Nutrition, pages 127-46 (2000).

In a further aspect, the invention provides for a use of lysine to prepare a composition that has a total lysine to metabolizable energy ratio of from about 6 to about 10 g/Mcal. As discussed above in the context of the methods, diets, and compositions of the invention, such composition is useful for promoting fat loss in an adult animal. In some embodiments, the composition is useful for promoting fat loss while maintaining the amount of the animal's lean muscle mass. In other embodiments, the composition is useful for promoting fat loss while increasing the amount of the animal's lean muscle mass.

In a further aspect, the invention provides an article of manufacture, for example, a kit for promoting fat loss in an adult animal. The kit comprises two or more ingredients that, when combined together and, optionally, with additional ingredients that are or are not a part of the kit, yield a composition of this invention. One of the two or more ingredients that are to be combined can be, for example, pure lysine or derivative thereof or a composition comprising lysine, and, optionally, additional amino acids. Another one of the two or more ingredients that are to be combined can be, for example, a food composition. If, to prepare a composition of the invention, additional ingredients that are not a part of the kit are needed, the kit provides instructions how to obtain and use those ingredients.

In some embodiments, the kit further comprises an agent for increasing lean muscle mass, reducing fat gain, and/or promoting the health or wellness of the animal. Suitable agents are discussed above in the context of the method for promoting fat loss of the invention.

In some embodiments, the kit further comprises instructions for one or more of (1) preparing a composition of the invention by combining the two or more ingredients and, optionally, additional ingredients that are or are not a part of the kit, (2) feeding a diet or composition of the invention to the adult animal to promote fat loss, (3) administering an agent for increasing lean muscle mass, reducing fat gain, and/or promoting the health or wellness of the animal to the animal in conjunction with feeding the animal a diet or composition of this invention, (4) promoting fat loss in an adult animal by feeding the animal a diet or composition of the invention, and (5) promoting fat loss in an adult animal by administering to the animal an agent for increasing lean muscle mass, reducing fat gain, and/or promoting the health or wellness of the animal in conjunction with feeding the animal a diet or composition of the invention.

In some embodiments, the kit comprises in separate containers in a single package or in separate containers in a virtual package, as appropriate, a composition that has a total lysine to metabolizable ratio of from about 6 to about 10 g/Mcal, or two or more ingredients, that, when combined together and, optionally, with additional ingredients that are or are not a part of the kit, yield a composition that has a total lysine to metabolizable ratio of from about 6 to about 10 g/Mcal, and one or more of (1) instructions for feeding the composition to the animal, (2) instructions for making the composition by combining the ingredients, (3) one or more agents for increasing lean muscle mass, reducing fat gain, and/or promoting the health or wellness of the animal, and (4) instructions for administering the agent(s) in conjunction with feeding the composition.

The term "single package" generally means that the components of a kit are physically associated in or with one or more containers and considered as a unit of manufacture, distribution, sale, or use. Containers include, for example, bags, boxes, bottles, shrink wrap packages, stapled or otherwise fixed components, and combinations thereof. A single package can be, for example, containers or individual food compositions physically associated such that they are considered a unit for manufacture, distribution, sale, or use. The term "virtual package" generally means that the components of a kit are associated by directions on one or more physical or virtual kit components instructing the user how to obtain additional components, e.g., in a bag containing one component and directions instructing the user to go to a website, contact a recorded message, view a visual message, or contact a caregiver to obtain instructions on how to use the kit. When the kit comprises a virtual package, the kit is limited to instructions in a virtual environment with one or more physical kit components.

In a further aspect, this invention provides a means for communicating information about or instructions for (1) using a diet, composition, and/or kit of this invention to promote fat loss in an adult animal, or (2) using one or more agents for increasing lean muscle mass, reducing fat gain, and/or promoting health or wellness of an adult animal in conjunction with a diet or composition of this invention, the means comprising a document, digital storage media, audio presentation, or visual display containing the information or instructions. In some embodiments, the communicating means comprises a document, digital storage media, optical storage media, audio presentation, or visual display containing the information or instructions. Preferably, the communication means is a displayed web site or a brochure, product label, package insert, advertisement, or visual display containing such information or instructions. Useful information or instructions include, for example, (1) information and instructions how to use a composition, method, or kit of the invention and (2) contact information for animal caregivers if they have a question about the invention and its uses.

Unless otherwise stated, all percentages expressed herein are weight percentages on a dry matter basis. The term "dry matter basis" (DMB) means that an ingredient's concentration in a composition is measured after any moisture in the composition has been removed.

The invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise. Similarly, the words "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

All patents, patent applications, and other references mentioned herein are incorporated herein by reference to the extent allowed by law for the purpose of describing and disclosing the compounds, processes, techniques, procedures, technology, articles, and other compositions and methods disclosed therein that might be used with the present invention. However, nothing herein is to be construed as an admission that the invention is not entitled to antedate such disclosure by virtue of prior invention.

EXAMPLES

The invention can be further illustrated by the following examples of preferred embodiments thereof, although it will be understood that these examples are included merely for purposes of illustration and are not intended to limit the scope of the invention unless otherwise specifically indicated.

Example 1

24 dogs (average age 7 years) with greater than 37% body fat (of total weight) are divided into 3 groups and then fed Food A, B, or C, respectively, for 3 months unless optimal weight (i.e., 20% body fat) is achieved earlier. Foods A, B, C are formulated as dry dog foods meeting AAFCO's minimum nutrient requirements for maintenance. The results from the nutrient analysis of Foods A, B, and C are presented in Table 1. Food A is a control high fiber, low fat food.

TABLE 1

Nutrient Analysis of Foods A, B, and C

| Nutrient | Units | Food A | Food B | Food C |
|---|---|---|---|---|
| Crude Protein | % DMB | 24.9 | 34.0 | 50.4 |
| Crude Fat | % DMB | 7.9 | 18.2 | 18.8 |
| Crude Fiber | % DMB | 21.1 | 3.0 | 1.6 |
| Ash | % DMB | 5.1 | 4.8 | 5.3 |
| Calcium | % DMB | 0.91 | 0.70 | 0.84 |
| Phosphorus | % DMB | 0.64 | 0.63 | 0.78 |
| Carnitine | ppm | 300 | 300 | 300 |
| Lysine | % DMB | 1.43 | 2.62 | 2.95 |
| Arginine:Lysine ratio | — | 1.07 | 0.78 | 0.96 |
| Leucine:Lysine ratio | — | 1.42 | 1.07 | 1.75 |
| Isoleucine:Lysine ratio | — | 0.73 | 0.43 | 0.62 |
| Valine:Lysine ratio | — | 0.88 | 0.57 | 0.78 |
| Predicted Metabolizable Energy (Atwater) | kcal/kg | 2938 | 4087 | 4287 |
| Lysine: Predicted Metabolizable Energy | g/Mcal | 4.9 | 6.4 | 6.9 |

TABLE 1-continued

Nutrient Analysis of Foods A, B, and C

| Nutrient | Units | Food A | Food B | Food C |
|---|---|---|---|---|
| Actual Metabolizable Energy | kcal/kg | 2940 | 4340 | 4669 |
| Lysine: Actual Metabolizable Energy | g/Mcal | 4.86 | 6.04 | 6.32 |

The average daily intakes are 269 g for Food A, 193 g for Food B, and 169 g for Food C. All dogs undergo dual energy x-ray absorptiometry (DEXA) as well as chemistry screen analysis at 0, 30, 60, and 90 days. The DEXA results are presented in Tables 2 and 3. These results demonstrate that feeding an animal a diet that has a total lysine to metabolizable energy ratio that is about 6 g/Mcal or higher results in weight and fat loss. The results also demonstrate that such a diet does not require energy dilution (i.e., there is no need to increase the amount of fiber in the animal's diet to achieve weight or fat loss). The results further demonstrate that the total lysine to metabolizable energy ratio is independent from the protein to metabolizable energy ratio and that total lysine to metabolizable energy ratio of about 6 g/Mcal or higher can be achieved at various protein concentrations.

TABLE 2

Body Weight of Dogs Fed Foods A, B, and C

| Parameter | Units | Food A | Food B | Food C |
|---|---|---|---|---|
| Weight at day 0 | g | 17257 | 18091 | 16971 |
| Weight at day 30 | g | 15798 | 16675 | 15663 |
| Weight at day 60 | g | 14715 | 16013 | 14904 |
| Weight at day 90 | g | 13791 | 15469 | 14330 |
| Weight change from day 0 to day 30 | g | −1459 | −1317 | −1308 |
| Weight change from day 0 to day 60 | g | −2542 | −2078 | −2066 |
| Weight change from day 0 to day 90 | g | −3466 | −2622 | −2640 |
| Average weight change per day | g | −38.5 | −29.1 | −29.3 |

TABLE 3

Body Composition of Dogs Fed Foods A, B, and C

| Parameter | Units | Food A | Food B | Food C |
|---|---|---|---|---|
| Lean at day 0 | g | 9434 | 9920 | 9277 |
| Lean at day 30 | g | 9295 | 9500 | 9104 |
| Lean at day 60 | g | 9303 | 9625 | 9244 |
| Lean at day 90 | g | 9367 | 9786 | 9374 |
| Lean change from day 0 to day 30 | g | −138 | −420 | −173 |
| Lean change from day 0 to day 60 | g | −131 | −295 | −33 |
| Lean change from day 0 to day 90 | g | −67 | −134 | +97 |
| Average lean change per day | g | −0.74 | −9.57 | +1.08 |
| Fat at day 0 | g | 7343 | 7669 | 7198 |
| Fat at day 30 | g | 6028 | 6770 | 6065 |
| Fat at day 60 | g | 4952 | 5899 | 5181 |
| Fat at day 90 | g | 2631 | 5206 | 4487 |
| Fat change from day 0 to day 30 | g | −1314 | −899 | −1133 |
| Fat change from day 0 to day 60 | g | −2390 | −1770 | −2017 |
| Fat change from day 0 to day 90 | g | −4711 | −2463 | −2711 |
| Average fat change per day | g | −52.4 | −27.4 | −30.1 |

In the specification, there have been disclosed typical preferred embodiments of the invention and, although specific terms are employed, they are used in a generic and descriptive sense only and not for purposes of limitation, the scope of the invention being set forth in the claims. Obviously many modifications and variations of the invention are possible in light of the above teachings. It is therefore to be understood that within the scope of the appended claims the invention may be practiced otherwise than as specifically described.

What is claimed is:

1. A composition for promoting fat loss in an adult canine or feline wherein the composition is a food composition and comprises (1) a total lysine to metabolizable energy ratio of from 6 to about 10 g/Mcal and (2) leucine in a total leucine to total lysine ratio of from about 0.9 to about 2.2.

2. The composition of claim 1 wherein the composition comprises arginine in a total arginine to total lysine ratio of from about 0.6 to about 1.4.

3. The composition of claim 1 wherein the composition comprises isoleucine in a total isoleucine to total lysine ratio of from about 0.2 to about 1.

4. The composition of claim 1 wherein the composition comprises valine in a total valine to total lysine ratio of from about 0.4 to about 1.2.

5. The composition of claim 1 wherein the composition comprises arginine, leucine, isoleucine, and valine in a total arginine plus leucine plus isoleucine plus valine to total lysine ratio of from about 3 to about 6.

* * * * *